(12) United States Patent
Kieninger

(10) Patent No.: US 10,864,529 B2
(45) Date of Patent: Dec. 15, 2020

(54) METHOD AND DEVICE FOR TREATING A MIXTURE OF EXPANSION GAS AND FILLING PRODUCT FOAM IN A BEVERAGE FILLING PLANT

(71) Applicant: KRONES AG, Neutraubling (DE)

(72) Inventor: Stefan Kieninger, Neutraubling (DE)

(73) Assignee: Krones AG, Neutraubling (DE)

( * ) Notice: Subject to any disclaimer, the term of this patent is extended or adjusted under 35 U.S.C. 154(b) by 187 days.

(21) Appl. No.: 16/230,897

(22) Filed: Dec. 21, 2018

(65) Prior Publication Data

US 2019/0143344 A1   May 16, 2019

Related U.S. Application Data

(62) Division of application No. 15/537,345, filed as application No. PCT/EP2015/080160 on Dec. 17, 2015, now Pat. No. 10,478,832.

(30) Foreign Application Priority Data

Dec. 17, 2014   (DE) ........................ 10 2014 118 815

(51) Int. Cl.
  *B67C 3/06*   (2006.01)
  *B67C 3/10*   (2006.01)
  *B01F 3/04*   (2006.01)
  *B01D 19/02*  (2006.01)
  *B04C 9/00*   (2006.01)
  (Continued)

(52) U.S. Cl.
  CPC   *B04C 9/00* (2013.01); *A23L 2/76* (2013.01); *A61L 2/18* (2013.01); *B01D 19/0036* (2013.01); *B01D 19/0057* (2013.01); *B01D 19/02* (2013.01); *B01D 19/0404* (2013.01); *B01F 3/04099* (2013.01); *B04C 5/04* (2013.01); *B04C 5/23* (2013.01); *B08B 9/0813* (2013.01); *B67C 3/06* (2013.01); *B67C 3/10* (2013.01); *B67C 3/22* (2013.01); *A23V 2002/00* (2013.01);
  (Continued)

(58) Field of Classification Search
  CPC .......... B01F 3/04; B01F 3/04099; B67C 3/06; B67C 3/10; B01D 19/02
  See application file for complete search history.

(56) References Cited

U.S. PATENT DOCUMENTS

| 1,345,437 | A | 7/1920 | Fehr |
| 2,792,029 | A | 5/1957 | Riedel |
| 6,192,946 | B1 * | 2/2001 | Clusserath ................ B67C 3/12 |
| | | | 141/40 |

FOREIGN PATENT DOCUMENTS

| CN | 1938100 | 3/2007 |
| CN | 201276211 | 7/2009 |

(Continued)

OTHER PUBLICATIONS

PCT Application No. PCT/EP2015/080160, International Search Report, dated Mar. 10, 2016, 4 pages.

(Continued)

*Primary Examiner* — Robert A Hopkins
(74) *Attorney, Agent, or Firm* — Haynes and Boone, LLP

(57) ABSTRACT

Various embodiments relate to devices and methods for treating a mixture of expansion gas and filling product foam in a beverage filling plant, comprising the steps of introducing the mixture of expansion gas and filling product foam into a closed separation container and extracting the expansion gas out of the closed separation container via suction.

10 Claims, 3 Drawing Sheets

(51) Int. Cl.
- *B67C 3/22* (2006.01)
- *B01D 19/00* (2006.01)
- *B08B 9/08* (2006.01)
- *A61L 2/18* (2006.01)
- *A23L 2/76* (2006.01)
- *B01D 19/04* (2006.01)
- *B04C 5/04* (2006.01)
- *B04C 5/23* (2006.01)
- *B67C 3/08* (2006.01)

(52) U.S. Cl.
CPC .. *B04C 2009/005* (2013.01); *B04C 2009/008* (2013.01); *B67C 3/08* (2013.01); *B67C 3/222* (2013.01)

(56) References Cited

FOREIGN PATENT DOCUMENTS

| | | |
|---|---|---|
| CN | 101564607 | 10/2009 |
| CN | 101639422 | 2/2010 |
| CN | 202366707 | 8/2012 |
| CN | 202686856 | 1/2013 |
| CN | 202983294 | 6/2013 |
| CN | 103402597 | 11/2013 |
| CN | 103446869 | 12/2013 |
| CN | 103803469 | 5/2014 |
| DE | 312484 | 5/1919 |
| DE | 1129078 | 5/1962 |
| DE | 3930593 | 3/1991 |
| DE | 19606464 | 8/1997 |
| DE | 102010031729 | 6/2011 |
| EP | 1308502 | 5/2003 |
| EP | 1693442 | 8/2006 |
| JP | 2001276506 | 10/2001 |
| JP | 2008155941 | 7/2008 |

OTHER PUBLICATIONS

Chinese Office Action, Chinese Patent Application No. 201580069454.7, dated Sep. 6, 2018, 12 pages.
Chinese Office Action, Chinese Patent Application No. 201580069454.7, dated Apr. 28, 2019, 9 pages.

\* cited by examiner

METHOD AND DEVICE FOR TREATING A MIXTURE OF EXPANSION GAS AND FILLING PRODUCT FOAM IN A BEVERAGE FILLING PLANT

CROSS-REFERENCE TO RELATED APPLICATIONS

This application is a divisional of U.S. patent application Ser. No. 15/537,345 filed Jun. 16, 2017, which is a U.S. National Stage application under 35 U.S.C. § 371 of International Application No. PCT/EP2015/080160 filed Dec. 17, 2015, which claims priority to German Patent Application No. DE 10 2014 118 815.2 filed Dec. 17, 2014, the contents of each of which are hereby incorporated by reference in their entirety.

TECHNICAL FIELD

The present invention relates to a device and a method for treating a mixture of expansion gas and fill product foam in a beverage filling plant, for example, treating a mixture of $CO_2$ and beer foam.

BACKGROUND OF THE INVENTION

It is known in beverage filling plants to fill carbonated beverages using the counter-pressure method, in which, prior to the actual filling with the fill product, the container to be filled is pre-pressurized with a pressure gas, and the carbonated fill product is then introduced into the container to be filled, which has been pre-pressurized in this manner and is hence under pressure. Through the application of the pre-pressure to the container, during the filling process there is no excessive release, or no release at all, of the $CO_2$ that is present in the fill product, so that in this manner excessive foaming of the fill product can be prevented. The filling process can thereby be carried out quickly and precisely, since the end of the filling process, for example, when a predetermined fill height is reached, can be determined precisely using a fill level probe due to the substantial absence of fill product foam. Accordingly, a carbonated fill product can be filled quickly and precisely in this manner.

After the actual filling process, when all fill product is accommodated in the now filled container, the container is still at an overpressure. In particular, the head space of the container contains gas under pressure, which is substantially a mixture of the $CO_2$ that is present in the carbonated fill product and the pre-pressurization gas. When the pre-pressurization gas is also $CO_2$, the gas present in the head space is thus substantially $CO_2$ under pressure.

Before the container can be conveyed to a further processing step, for example, a capper, it must be detached from the applicable filling element. Prior to this, the overpressure in the head space of the container must accordingly be relieved. For this purpose, the overpressure is relieved in a controlled manner by opening a relief valve. The opening of the relief valve establishes a fluid communication via a relief line between the head space of the container and the surrounding area, such that the overpressure present in the head space of the container can be relieved into the surrounding area when the relief valve is opened.

In the case of carbonated beverages, however, this leads to foaming of the fill product because the rapid relief of pressure in the head space causes spontaneous release of $CO_2$ from the fill product to take place. This tendency to foam is particularly pronounced when beer is filled. The foam that arises in this way can then pass through the relief valve together with the expansion gas and enter the relief channel, through which it gradually travels. The mixture of expansion gas and fill product foam that is thereby present in the relief channel escapes from the end of the relief channel in an uncontrolled manner. At the end of the relief channel, the fill product foam usually drips onto the floor of the filling hall or into a gully.

The concentrations of the expansion gas, for example, $CO_2$, that arise in the filling hall are in some cases undesirable.

SUMMARY

Proceeding from the known state of the art, an improved method and corresponding device are provided for treating a mixture of expansion gas and fill product foam in a beverage filling plant.

In one embodiment, treating a mixture of expansion gas and fill product foam in a beverage filling plant is performed with the features of claim 1. Advantageous further developments of the method arise from the dependent claims, from this description, and from the figures.

Accordingly, a method for treating a mixture of expansion gas and fill product foam in a beverage filling plant is disclosed. The method includes introducing the mixture of expansion gas and fill product foam into a closed separation container and extracting the expansion gas out of the closed separation container via suction.

The mixture of expansion gas and fill product foam is introduced into a closed separation container and the expansion gas is extracted from the separation container, such that: firstly, contamination of the area surrounding the beverage filling plant by the expansion gas is avoided, and thus impairment of the health of filling plant staff due to the expansion gas can be reduced or avoided; and secondly, contamination of the area surrounding the beverage filling plant with fill product foam can be avoided due to the closed design of the separation container.

Accordingly, there is a reduction in contamination, by both the expansion gas and the fill product foam, of the area directly surrounding the beverage filling plant. Thus, impairment of the health of staff can be reduced, and a filling process that is altogether more hygienic and more aesthetically acceptable is made possible.

In one exemplary embodiment of the method, a fluid medium is applied by sprinkling to the mixture of expansion gas and fill product foam that is introduced into the closed separation container. Application of the fluid medium achieves the suppression and liquefaction of the fill product foam in the separation container, and accordingly prevents suction of the fill product foam into the suction extractor and out of the closed separation container.

In a further exemplary embodiment of the method, in order to sprinkle the mixture of expansion gas and fill product foam, the fluid medium is extracted from the closed separation container from, for example, a lower area of the closed separation container and the fluid medium is recirculated.

In this manner, through recirculation, it is possible in an economically and environmentally favorable manner to sprinkle the mixture of expansion gas and fill product foam continuously, uniformly, periodically or as required, such that restriction of the fill product foam within the closed separation container to a low level can be reliably achieved. In addition, through the recirculation of the fluid, an economical design is achieved, since a constant supply of fresh water is unnecessary, and instead the fluid medium can be reused for sprinkling.

In a lower area, for example, a sump, of the closed separation container, a fluid medium can be provided, which can then be extracted for sprinkling the mixture of expansion gas and fill product foam in the manner described above.

The fluid medium can originally be a supply of fresh water. Throughout treatment of the mixture of expansion gas and fill product foam, the fluid medium is increasingly mixed with components of the fill product from the suppressed and liquefied fill product foam.

The fluid medium from the closed separation container, together with the fill product foam that has been liquefied by sprinkling, can be conveyed out of the closed separation container continuously, periodically or as required. If it is removed as required, this can be initiated, for example, when a time condition is satisfied or when a fill height of the fluid medium in the closed separation container is reached, such that when a specified fill height is reached, the excess fluid is extracted from the closed separation container. The fluid that is removed can, for example, be conveyed to a waste water pipe.

In order to achieve an efficient separation of the fill product foam, or the fill product components, from the mixture of expansion gas and fill product foam as soon as it enters the closed separation container, the inflow of the mixture of expansion gas and fill product foam can take place tangentially in a cylindrical or conical separation container, such that, due to the centrifugal forces in effect, there occurs a first displacement of the fill product foam to the interior wall of the closed separation container, and thereby a separation of expansion gas and fill product foam.

In the closed separation container, the expansion gas can be extracted via suction above the sprinkler, so that it is possible to avoid the fill product foam being sucked in by the suction extractor.

In another exemplary embodiment of the present invention, for the purpose of cleaning, a cleaning and/or sterilization medium is introduced into the closed separation container and subsequently conducted out of it, wherein the cleaning and/or sterilization medium is sprayed onto the interior wall of the closed separation container, and conducted out of the closed separation container in its lower area. In this manner, hygienic cleaning of the separation container can be achieved. Further, a clean-in-place (CIP) medium can also be conveyed through a relief channel to a filler valve, and/or from the filler valve through the relief channel into the closed separation container.

The term "closed separation container" is understood here to mean that it has no direct connection with its surrounding area. Instead, the conveying of media and fluids into the closed separation container, and the conveying of media and fluids out of the closed separation container, take place only in a controlled manner via suitable pipework.

Accordingly, the mixture of expansion gas and filling product foam is conveyed in a controlled manner within a closed system, and furthermore, the expansion gas is also conveyed in a controlled manner within a closed flow, so that the expansion gas can be, for example, dissipated in a controlled manner via a chimney without the expansion gas entering the filling hall.

In another embodiment, a device with the features of claim 9 is used for treating a mixture of expansion gas and fill product foam in a beverage filling plant. Advantageous further developments arise from the dependent claims.

In one exemplary embodiment, a device for treating a mixture of expansion gas and fill product foam in a beverage filling plant comprises a closed separation container into which a relief line which conveys the mixture of expansion gas and fill product foam discharges, wherein the expansion gas is extracted via suction from the separation container through a suction extractor. According to the embodiment, the separation container is closed.

This results in the same advantageous effects as those described above in connection with the method.

In one embodiment, a sprinkler nozzle is provided in the closed separation container, where the sprinkler nozzle applies a fluid medium to the mixture of expansion gas and fill product foam that is present in the closed separation container. Sprinkling can achieve the suppression, destruction or liquefaction of the fill product foam in the closed separation container.

In one embodiment, an outlet is provided in a lower area, for example, a sump, of the closed separation container, and the outlet is in fluid communication with the sprinkler nozzle, so that the fluid medium can be pumped in circulation from the lower area of the closed separation container to the sprinkler nozzle.

In one embodiment, a suction extractor for extracting the expansion gas is provided in fluid communication with the closed separation container, and is disposed above the sprinkler nozzle.

In one embodiment, the closed separation container is substantially cylindrical and/or conical in design, and the relief line is tangentially introduced into the closed separation container.

In one embodiment, a CIP nozzle is provided in the closed separation container to impinge on the interior wall of the closed separation container, and a lower area of the closed separation container is in fluid communication with a CIP return line.

BRIEF DESCRIPTION OF THE DRAWINGS

Further exemplary embodiments of the invention are more fully explained by the description below of the figures. The figures show.

DETAILED DESCRIPTION

Example embodiments are described below with the aid of the figures. In the figures, elements which are identical or similar, or have identical effects, are designated with identical reference signs. In order to avoid redundancy, repeated description of these elements is in part dispensed with in the description below.

Figure 1:
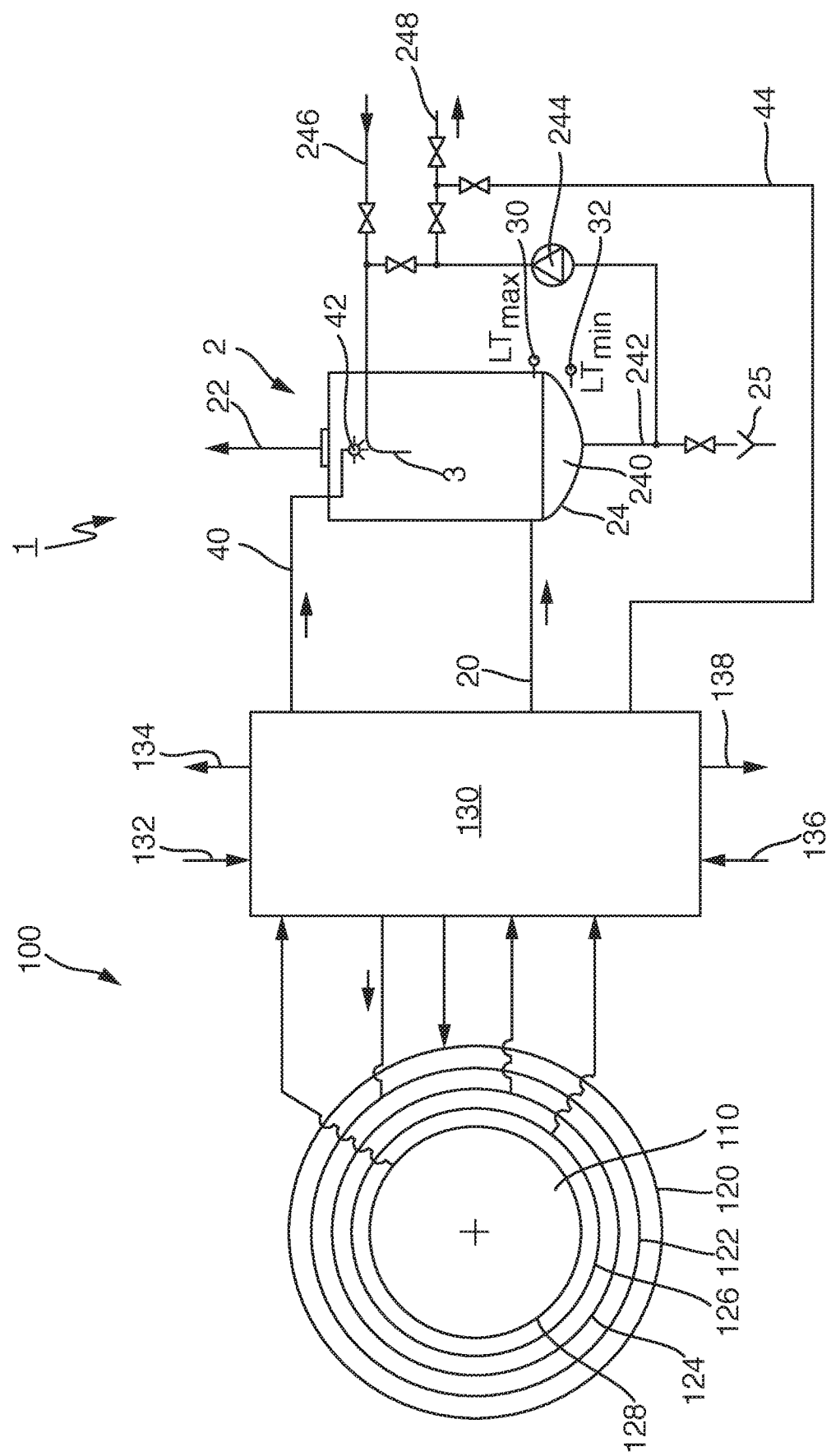
FIG. 1 is a schematic representation of a beverage filling plant with a filler carousel, a valve cluster and a device for treating a mixture of an expansion gas and fill product foam with a closed separation container.

FIG. 1 shows schematically a beverage filling plant 100 with a schematically indicated filler carousel 110 which has rotary medium distributor channels 120 to 128 (also indicated schematically), which are provided to deliver media from the stationary part of the beverage filling plant to the rotating filler carousel 110.

The outer rotary medium distributor channel 120 is provided for supplying fill product and—during the cleaning and sterilization of the beverage filling plant 100—cleaning and sterilization medium to the filler carousel 110. The second rotary medium distributor channel 122 is provided for supplying CO2 as rinsing gas and/or as pressurization gas. The third rotary medium distributor channel 124 is provided as a relief channel for relieving pressure in the head space of each filled container after filling, and accordingly transports a mixture of the expansion gas (e.g., CO2) and fill product foam that is carried along with the expansion gas.

A further rotary medium distributor channel 126 is provided for creating a vacuum or an underpressure, which is provided for switching the filler valve and/or for evacuating the container to be filled prior to filling. A further rotary medium distributor channel 128 is provided as a clean-in-place (CIP) return flow line for CIP cleaning or sterilization.

The supply and/or discharge, as well as the control of the supply of each medium to the rotary medium distributor and the corresponding rotary medium distributor channels 120 to 128, takes place via a valve cluster 130, which in the example embodiment shown is provided in the stationary part of the beverage filling plant 100, and which can charge the rotary medium distributor channels 120 to 128 with the applicable media in a controlled manner.

The fill product, or—during cleaning or sterilization—a cleaning or sterilization medium in the form of a CIP medium, flows via a fill product intake 132 into the valve cluster 130. A CIP return flow line 134 is provided, through which the CIP medium can accordingly be returned to a CIP station during cleaning or sterilization in order to process or replace the CIP medium. Gaseous CO2 is also supplied to the valve cluster 130 via a CO2 supply line 136, in order to use this gas as a pre-pressurizing and rinsing medium in the container to be filled. A vacuum connection 138 is further provided, through which a vacuum can be provided in a switchable manner in the valve cluster 130.

A device 1 for treating a mixture of expansion gas and fill product foam is also provided in the beverage filling plant 100. The mixture of expansion gas and fill product foam is supplied to the device 1 via a relief line 20. The relief line 20 thus conveys both the expansion gas and the fill product foam that is carried along by the expansion gas.

The device 1 comprises a closed separation container 2, into which a mixture of expansion gas (e.g., CO2) and fill product foam is introduced from the valve cluster 130 via the relief line 20, when, in the course of the relief of pressure in the head space of a filled container, expansion gas is discharged in a controlled manner via the valve cluster 130, and fill product foam is thereby carried along.

The separation container 2 may be substantially cylindrical or conical in design, and the relief line 20 discharges into the closed separation container 2, for example, into a lower area of the closed separation container 2 and tangentially.

Because the separation container 2 is, for example, substantially cylindrical or conical in design, when the mixture of expansion gas and fill product foam is introduced tangentially via the relief line 20, depositing of the fill product foam on the interior wall of the closed separation container 2 can be achieved by centrifugal forces alone.

The expansion gas (e.g., CO2) can be extracted from the upper area of the closed separation container 2 by a suction extractor 22.

Through the provision of the closed separation container 2 in combination with the suction extractor 22, it is possible to avoid the formation of an increased concentration of expansion gas, for example, an increased concentration of CO2, in the area of the beverage filling plant 100, which could damage or impair the health of staff at the beverage filling plant 100. The suction extractor 22 thereby may extract the expansion gas via suction into an exterior area located at a distance from the beverage filling plant 100, and convey the expansion gas through a chimney, or through a fan via the roof of the hall or another area, out of the room in which the beverage filling plant 100 is disposed.

In the lower area of the closed separation container 2, a sump 24 is provided, which in the schematically shown example embodiment is filled with a fluid medium 240. At the beginning of the treatment of the mixture of expansion gas and fill product foam, the fluid medium 240 is, for example, fresh water. During the separation of the fill product foam, however, the fresh water is mixed with components of the fill product which have been transported by the fill product foam into the closed separation container 2.

At the lowest position on the closed separation container 2, for example, its sump 24, an outlet 242 is provided, via which the fluid medium 240 can be extracted from the closed separation container 2. The fluid medium 240 is pumped by a pump 244 into a sprinkler nozzle 3, so that the fluid medium 240 is sprinkled onto the mixture of expansion gas and fill product foam that is present in the closed separation container 2. By sprinkling of the mixture of expansion gas and fill product foam, the fill product foam in the closed container is suppressed, and the bubbles in the fill product foam are progressively burst, so that the fill product foam is substantially liquefied.

Via the outlet 242 provided in the lower area of the closed separation container 2 and the pump 244, the fluid medium 240 can thus be sprinkled on the fill product foam that accumulates in the closed separation container 2. Accordingly, the fill product foam supplied via the relief line 20 is sprinkled in such a manner that the fill product foam can be suppressed and an excessive rise in the level of the fill product foam in the closed separation container 2 can be prevented, such that it is possible to prevent the fill product foam from being sucked in by the suction extractor 22 for the expansion gas.

The sprinkling of the fill product foam through the sprinkler nozzle 3 further achieves the destruction of the fill product foam, and accordingly only the components of the fill product that are transported by the fill product foam are present, in liquid or particulate form, and are collected in the sump 24.

Via a fresh water supply line 246, the sprinkler nozzle 3 can also be fed with fresh water. This is in particular carried out when the sump 24 is to be refilled with fluid medium 240, for example, at the beginning of each treatment procedure.

In order to carry out the method for treating a mixture of expansion gas and fill product foam, a mixture of the fill product foam and the expansion gas is accordingly introduced via the relief line 20 into the closed separation container 2. At the same time, through the sprinkler nozzle 3, a fluid medium 240 is applied to the fill product foam that accumulates in the closed separation container 2, in order thereby to suppress or destroy the foam. The fluid medium 240 that is applied via the sprinkler nozzle 3, along with the components, or liquefying components, of the fill product foam that have been entrained by the fluid medium 240, flow into the sump 24. In contrast, the expansion gas is extracted via the suction extractor 22 from the closed separation container 2.

In order to avoid the sucking in, or extraction by sucking, of the fill product foam via the suction extractor 22, the suction extractor 22 is in fluid communication with the closed separation container 2, and the suction extractor 22 from the closed separation container 2 is disposed above the sprinkler nozzle 3.

When the fluid medium 240 in the sump 24 has reached a certain level, which is measured, for example, by an upper level detector 30 in the closed separation container 2 and/or by the satisfaction of a timing condition, the sump, and in particular the fluid medium 240 in the sump, is discharged via the pump 244 to a waste water pipe 248 through the operation of the appropriate valves. The pump 244 and the appropriate valves for transfer of the fluid medium 240 from the sump 24 to the waste water pipe 248 are kept open or in operation until a lower level detector 32 detects that the fluid medium 240 in the sump 24 has reached a level that is at or below a specified lower level. The previously opened valves are then closed and the valve for the sprinkler nozzle 3 is opened, so that the fluid medium 240 is again pumped from the sump 24 to the sprinkler nozzle 3, and accordingly circulated such that the mixture of expansion gas and fill product foam that has accumulated in the closed separation container 2 is again sprinkled with the fluid medium 240.

After production has finished, the sump 24 can be emptied fully into a gully 25, for example, by opening an appropriate valve.

There thus results an efficient method for treating a mixture of expansion gas and fill product foam in a beverage filling plant 100.

In order to carry out cleaning and sterilization of the beverage filling plant 100 after the production run has finished, a cleaning process is performed through a closed cleaning cycle. For this purpose, a cleaning or sterilization medium is supplied as a so-called CIP medium via the fill product intake 132 to the valve cluster 130 in the known manner, and then flows via the fill product rotary medium distributor channel 120 through the filler valve in order to clean or sterilize the filler valve itself. From the filler valve, the CIP medium is then conveyed via a CIP return line 128 back to the valve cluster 130.

Through a CIP supply line 40, the CIP medium can also be channeled from the filler valve cluster 130 to a CIP nozzle 42, which is disposed in the upper area of the closed separation container 2. The CIP nozzle 42 is, for example, designed as a 360° nozzle, so that the entire interior wall of the closed separation container 2 can be impinged with cleaning or sterilization medium. In this manner, the closed separation container 2 can be fully cleaned by impingement with the CIP medium. Via the outlet 242 and the pump 244, with appropriate switching of the valves, the CIP medium is returned via a CIP return line 44 to the valve cluster 130. The cleaning is thus carried out in a cycle with no medium discharged; instead, the cleaning medium is recirculated through the closed separation container 2 in the manner described above.

In an alternative or further embodiment, the CIP medium can also flow out of the valve cluster 130 into the closed separation container 2 via the relief line 20, in order to enable the cleaning of the relief line 20.

Figure 2:
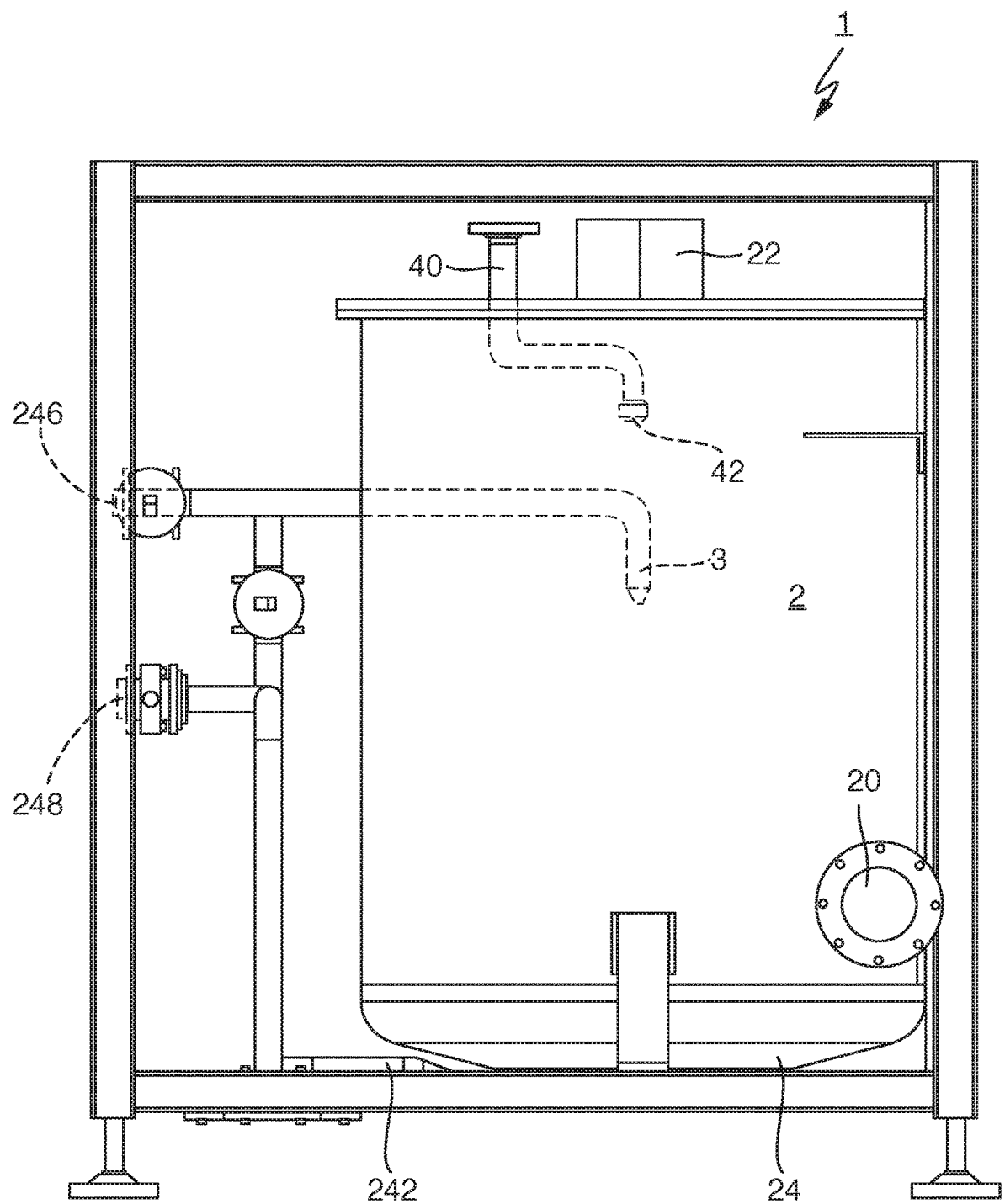
FIG. 2 is a schematic side representation of a device for treating a mixture of an expansion gas and fill product foam.

FIG. 2 shows schematically the closed separation container 2, in a schematic side representation, wherein the sprinkler nozzle 3 in the interior is shown by a broken line and the intake of the relief line 20 is also shown schematically. Additionally shown are the sump 24 in the lower area of the closed separation container 2, and the outlet 242. Via a waste water connection 248 and a fresh water connection 246, the closed separation container 2 can be supplied with fresh water and the waste water can be discharged.

A CIP supply line 40 along with the CIP nozzle 42 are shown, which are provided in the interior of the closed separation container 2, and which serve to clean or sterilize the interior wall of the closed separation container 2 in the manner described above.

Through the suction extractor 22 disposed in the upper area of the closed separation container, the expansion gas is extracted from the closed separation container 2.

Figure 3:
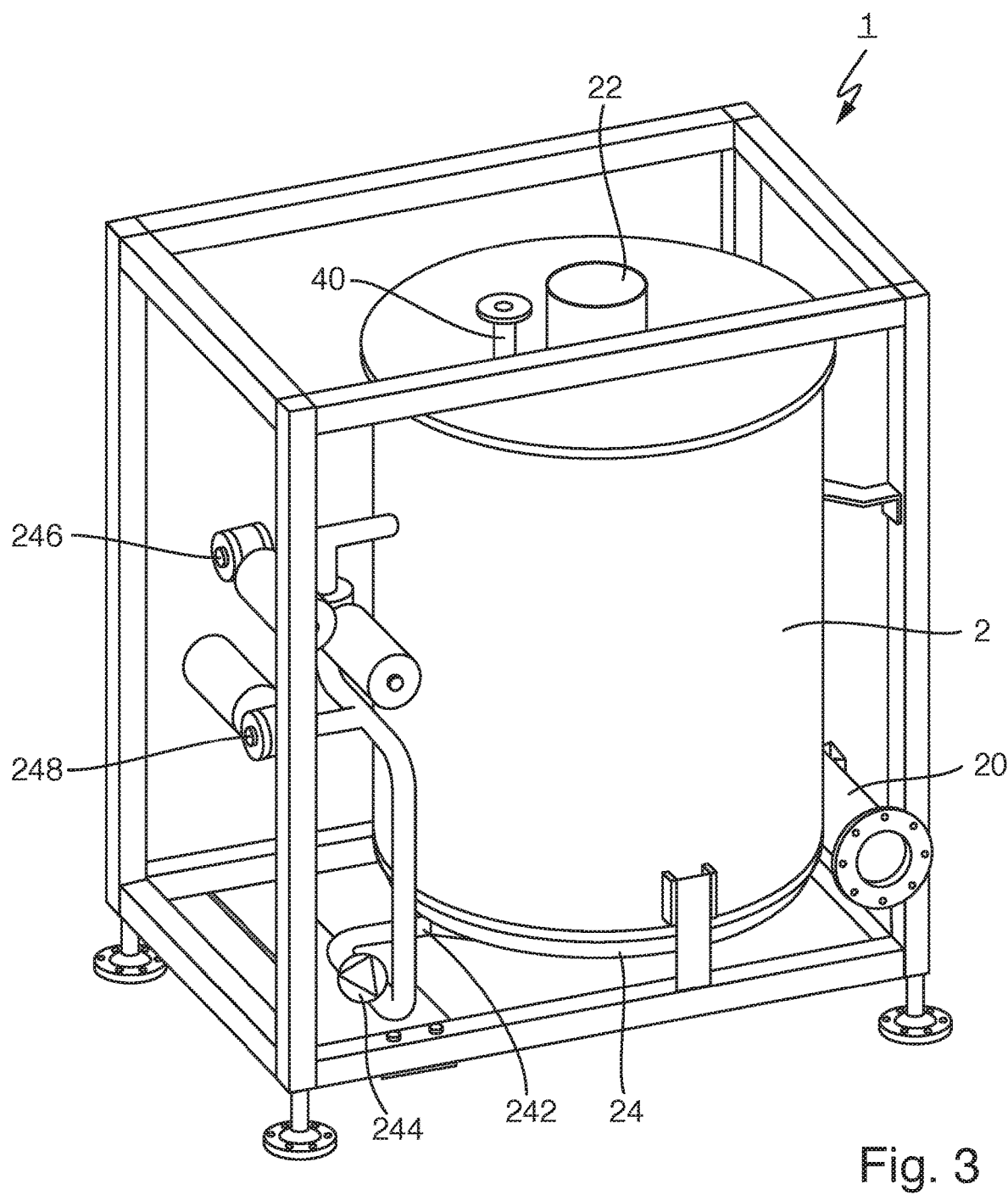
FIG. 3 is a schematic perspective representation of the device from FIG. 2.

FIG. 3 again shows the device of FIG. 2 in a schematic perspective view.

To the extent applicable, all individual features described in the example embodiments can be combined with each other and/or exchanged, without departing from the field of the invention.

LIST OF REFERENCE SIGNS 1 device for treating a mixture of expansion gas and fill product foam
100 beverage filling plant
110 filler carousel
120 fill product supply line
122 $CO_2$ supply line
124 $CO_2$ relief line
126 vacuum
128 CIP return line
130 valve cluster
132 fill product intake
134 CIP return flow line
136 $CO_2$ supply line
138 vacuum connection
2 closed separation container
20 relief line
22 suction extractor
24 sump
240 medium
242 outlet
244 pump
246 fresh water
248 waste water
25 gully
3 sprinkler nozzle
30 upper level detector
32 lower level detector
40 CIP supply line
42 CIP nozzle
44 CIP return line

What is claimed is:

1. A device for treating a mixture of an expansion gas and a fill product foam in a beverage filling plant, comprising:
a closed separation container configured to be coupled to a relief line to receive the mixture of the expansion gas and the fill product foam into the closed separation container and configured to be coupled to a suction extractor so that the expansion gas is extracted from the closed separation container via suction from the suction extractor.

2. The device of claim 1, further comprising a sprinkler nozzle disposed in the closed separation container, wherein the sprinkler nozzle applies a fluid medium to the mixture of the expansion gas and the fill product foam that is present in the closed separation container.

3. The device of claim 2, wherein a lower area of the closed separation container comprises an outlet.

4. The device of claim 3, wherein the outlet is in fluid communication with the sprinkler nozzle so that the fluid medium recirculated from the lower area of the closed separation container to the sprinkler nozzle.

5. The device of claim 3, wherein the lower area of the closed separation container comprises a sump.

6. The device of claim 2, further comprising the suction extractor, wherein the suction extractor is in fluid communication with the closed separation container and is disposed above the sprinkler nozzle.

7. The device of claim 1, wherein the closed separation container is at least substantially cylindrical and/or substantially conical.

8. The device of claim 1, further comprising the relief line, wherein the relief line is tangentially coupled to the closed separation container.

9. The device of claim 1, further comprising a clean-in-place (CIP) nozzle provided in the closed separation container, wherein the CIP nozzle is configured to impinge on an interior wall of the closed separation container with a CIP medium.

10. The device of claim 9, further comprising:
a CIP return line that is in fluid communication with a lower area of the closed separation container.

* * * * *